United States Patent
Coral et al.

[11] Patent Number: 6,122,554
[45] Date of Patent: Sep. 19, 2000

[54] ELECTRODE ASSEMBLY FOR ELECTROTHERAPY COMPRISING AN ADHERENT LAYER AND AN ABSORBENT COMPONENT FOR SUPPLYING WATER TO SAID ADHERENT LAYER

[75] Inventors: Hervé Coral, Le Landin; Patrick Hebert, Garcelles, both of France

[73] Assignee: Sport-Elec S.A., France

[21] Appl. No.: 09/120,404

[22] Filed: Jul. 22, 1998

[30] Foreign Application Priority Data

Jun. 3, 1998 [EP] European Pat. Off. ............ 98440117

[51] Int. Cl.[7] .............................. A61N 1/04; A61N 1/30
[52] U.S. Cl. .............................. 607/153; 607/115; 604/20
[58] Field of Search .............................. 604/20; 600/392, 600/391, 386, 372; 607/153, 115

[56] References Cited

U.S. PATENT DOCUMENTS

| | | | |
|---|---|---|---|
| 3,518,984 | 7/1970 | Mason | 600/392 |
| 4,319,579 | 3/1982 | Cartmell | 600/392 |
| 4,522,211 | 6/1985 | Bare et al. | 600/392 |
| 4,653,501 | 3/1987 | Cartmell et al. | 600/392 |
| 4,700,710 | 10/1987 | Hoffman | 600/392 |
| 4,827,939 | 5/1989 | Cartmell et al. | 600/392 |
| 5,158,537 | 10/1992 | Haak et al. | . |
| 5,310,404 | 5/1994 | Gyory et al. | . |
| 5,385,543 | 1/1995 | Haak et al. | . |
| 5,543,098 | 8/1996 | Myers et al. | . |

FOREIGN PATENT DOCUMENTS 0774272  6/1993  European Pat. Off. .

*Primary Examiner*—Kennedy J. Schaetzle
*Attorney, Agent, or Firm*—Ostrolenk, Faber, Gerb & Soffen, LLP

[57] ABSTRACT

An electrode assembly for electrotherapy which is usable with a DC current generator which offers divided or biphase emission. The aforementioned assembly contains a conductive component (1) covered with a layer (3) of an adherent material of hydrogel, as well as an absorbent component for supplying water to the adherent material during use of the assembly. The absorbent component is filled with water and is situated between the conductive component (1) and the layer (3) of adherent material of hydrogel, so as to store and supply water to the adherent hydrogel layer.

11 Claims, 2 Drawing Sheets

ELECTRODE ASSEMBLY FOR ELECTROTHERAPY COMPRISING AN ADHERENT LAYER AND AN ABSORBENT COMPONENT FOR SUPPLYING WATER TO SAID ADHERENT LAYER

BACKGROUND OF THE INVENTION

The present invention pertains to an electrode assembly for electrotherapy which is intended for use with a DC current generator offering divided or biphase emission.

Electrotherapy consists of use of electricity as a means of treatment, usually for providing stimulation of muscles, or, in the instance of ionotherapy, for enabling ionized active substances to enter the body.

Electrode assemblies which are used by therapists are usually supplied in the form of a component which contains an absorbent material and means of securing straps or similar items, thereby allowing encircling of the body so as to ensure attachment of the aforementioned component.

Electrode assemblies which are suitable for generators intended for use in the home usually consist of a flexible conductive component wherein the surface which is intended to come into contact with the skin is covered with a layer composed of a material which on the one hand allows the current to flow and on the other hand provides adherence to the skin.

The material covering the conductive component usually consists of a hydrogel which requires regeneration by supplying of water prior to use in each instance. In practical terms, a protective sheet covering the hydrogel layer must be removed, and the hydrogel layer must then be moistened with water, whereupon it is necessary to wait for a certain period of time for allowing complete absorption of the water by the hydrogel.

The steps which are required for the procedure whereby water is provided are relatively cumbersome because, on one hand, they cannot be performed in any location, and, on the other hand, it is difficult to handle the electrode after removal of the protective sheet.

Furthermore, in order for adhesive capability and low resistance to be maintained, the hydrogel must be maintained at a constant hydrometric level. Nevertheless, when the hydrogel is in contact with the skin and on account of increased heat created by transmission of the current, drying occurs.

An increase in resistance on account of drying of the hydrogel causes a decrease in power flowing from the generator to the skin through the electrode assembly, so that the user must seek to offset this phenomenon by increasing the power of the generator. This attempt to compensate is poorly tolerated, because the sensation of the current quickly becomes disagreeable on account of the fact that certain points, which are less "dry" than others, facilitate transmission of the current.

The intent of the present invention is to offer an electrode assembly which shall allow the various disadvantages to be overcome. Furthermore, it shall be suitable for use in ionotherapy.

An electrode assembly designed in accordance with the invention contains a conductive component covered with a layer of an adherent material of the hydrogel type, and it is essentially characterized by the fact that it contains items allowing a supply of water to said adherent material during use of the respective assembly.

According to a specific embodiment of an electrode assembly in accordance with the present invention, a component composed of an absorbent material which is intended to be impregnated with water is situated between the conductor and the layer of adherent material of the hydrogel type, thereby forming a means of storing water.

During use of an electrode assembly in accordance with the present invention, the adherent material of the hydrogel type draws water out of the absorbent component, so that it shall remain at a substantially constant hydrometric level.

According to an additional characteristic of an assembly in accordance with the invention, the layer of adherent material of the hydrogel type contains at least one opening situated to adjacent the absorbent component, thereby allowing said absorbent component to be impregnated with water prior to use.

According to another additional characteristic of the assembly in accordance with the invention, the layer of adherent material of the hydrogel type is covered with a protective sheet which contains openings opposite the opening or openings situated within said layer, thereby permitting filling of the absorbent component with water prior to use, without a need for removal of said protective sheet.

According to another embodiment of an electrode assembly according to the invention, this assembly includes a component composed of an absorbent material constituting a means of storing water, and this component is situated next to the conductor and is fitted into an area provided within the layer of adherent material of the hydrogel type.

According to an additional characteristic of this other embodiment of the assembly to which the invention pertains, the layer of adherent material of the hydrogel type is covered with a protective layer containing an opening opposite the area where the absorbent component is situated. This opening allows replacement of the absorbent component and/or supplying of water, without a need for removal of said protective sheet.

In accordance with the invention, an ionized active substance is added to the water intended to impregnate the absorbent component.

The advantages and characteristics of the present invention shall be more clearly understood in relation to the subsequent description which is based upon the appended sketches, where several embodiments are represented on a nonrestrictive basis.

DETAILED DESCRIPTION

Figure 1:
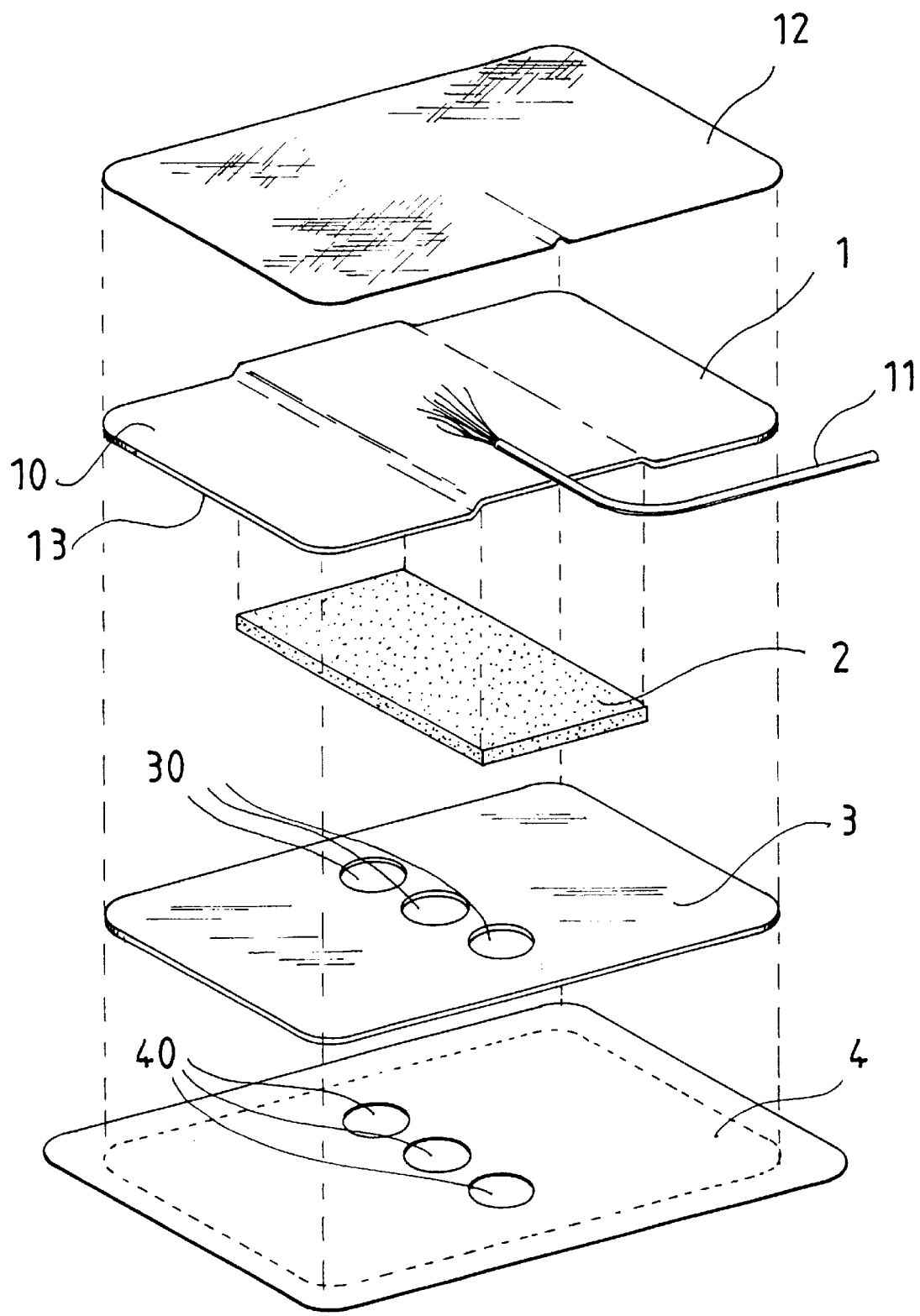
FIG. 1 represents an enlarged perspective view of an embodiment of an electrode assembly in accordance with the invention.

If FIG. 1 is examined, it is possible to observe that an electrode assembly in accordance with the invention includes a conductive component (1); which is preferably composed of carbon, with a lead (11) intended for connection with a current generator (not shown) placed in contact with the upper surface (10) of said conductive component.

It should be observed that the upper surface (10) and the conducting lead (11) are covered with a piece (12) of insulating material which can be produced from a material of the non-woven type.

A component (2) consisting of an absorbent material of the felt type, for example, is positioned against the bottom surface of the conductive component (1), which is supported by a layer (3) of a material which adheres to the skin, such as a hydrogel.

It should be observed that the dimensions of the item identified as (2) are less than those of the conductive component (1), and that the aforementioned item is situated within the middle portion of the latter component.

The layer identified as (3) is covered with a protective sheet (4) possessing larger dimensions in order to facilitate removal.

The aforementioned layer (3) contains three openings (30) situated adjacent to the absorbent component (2), whereas the protective sheet (4) also contains three openings (40) situated opposite the openings identified as (30), in such a manner that the absorbent component shall be accessible through the respective openings, (30) and (40).

In practical terms, the absorbent component (2) is to be impregnated with water, and this step can be completed easily by placing the electrode assembly beneath a tap. Then, by capillary action, the adherent material of the hydrogel type draws water out of the absorbent component, thereby allowing regeneration. Lastly, the protective sheet is removed, and the electrode assembly can be placed upon the skin.

During an electrotherapy procedure, the adherent material of the hydrogel type continues to draw water out of the absorbent component (2), in such a manner that drying does not occur, while the hydrometric level shall remain substantially constant.

In relation to electrodes reflecting prior art, the electrode assembly in accordance with the invention therefore requires fewer handling procedures for being positioned, and these procedures are easier.

Moreover, it is possible to include an ionized active product within the water, so as to allow performing of ionotherapy.

Figure 2:
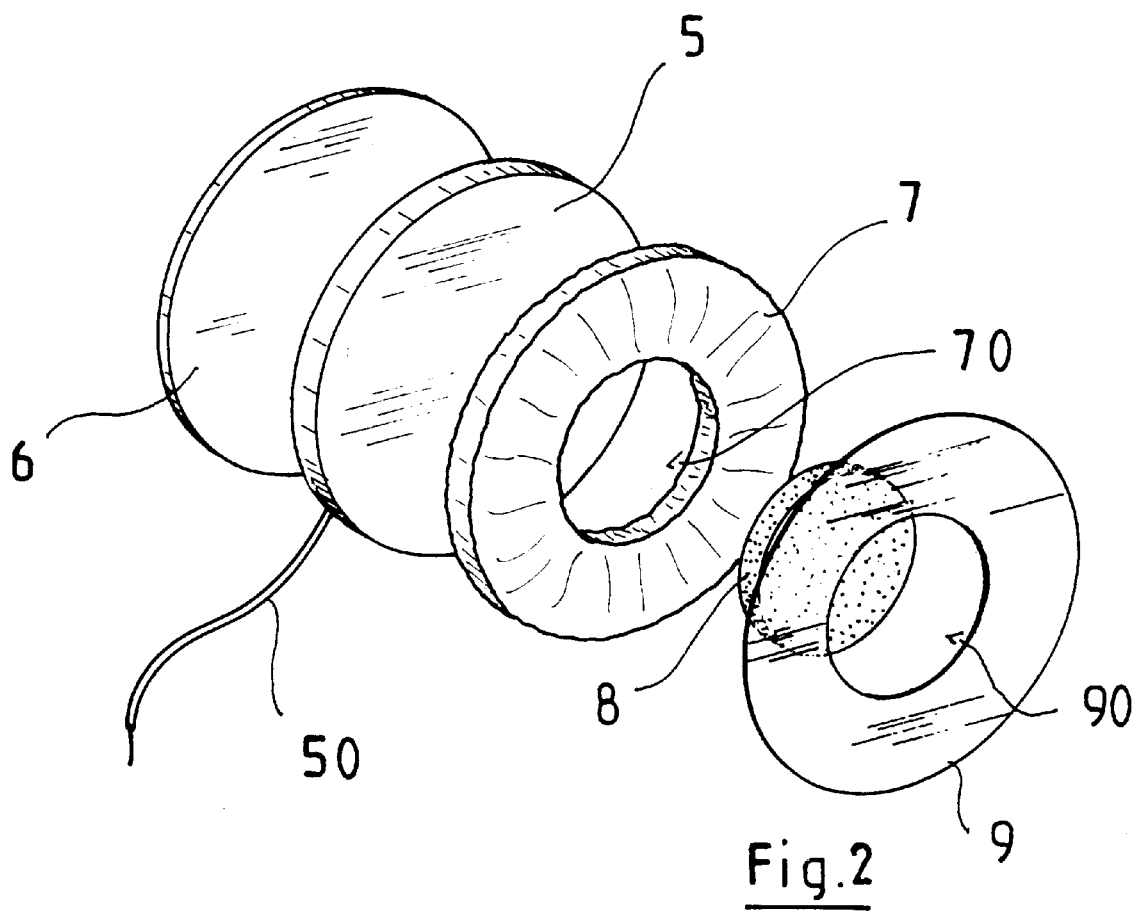
FIG. 2 represents an enlarged perspective view of another embodiment of an electrode assembly.

If FIG. 2 is consulted at this point, it is possible to observe that, in another embodiment of the assembly to which the invention pertains, this assembly likewise includes a conductive component (5) and a lead (50) covered with a means of insulation (6), a layer (7) composed of an adherent material of the hydrogel type, an absorbent component (8), and a protective sheet (9).

The layer (7) of adherent material of the hydrogel type contains an opening (70) where the absorbent component (8) possessing a complementary shape is to be positioned, while the protective sheet (9) contains an opening (90) situated opposite the opening identified as (70).

The absorbent component (8) shall be in contact with the conductive component (5), and, by means of its edges, it shall be in contact with the layer (7) of adherent material of the hydrogel type, in order to allow water to be supplied for this layer.

An electrode assembly designed in accordance with this second embodiment of the invention can be used in the same way as the first embodiment. On the other hand, it allows replacement of the absorbent component (8) by another of said components.

This configuration provides an advantage during performance of ionotherapy. Indeed, during successive ionization procedures, it is important that electrodes used for distributing an ionized product should not be reused for distributing a product with a different polarity. Furthermore, the possibility of removing and replacing the absorbent component identified as (8) allows use of components intended for one-time use.

Moreover, these absorbent components can be packaged in a form where they are pre-impregnated with an ionized active product and are ready for use, so as to eliminate errors in terms of levels of ionized substances, with the result that the active product shall be perfectly measured, whereby performing of ionotherapy by the general public can be allowed.

In addition, a text concerning use of the absorbent component can be placed upon the respective packaging. The aforementioned text can therefore include the nature of the product, locations for applying electrodes, the type of current which must be used, and the period of exposure.

It is possible for the electrode assembly designed in accordance with the present invention to be used not only by the general public, but also by therapists.

We claim:

1. An electrode assembly for electrotherapy, comprising:
   a conductive component;
   adjacent thereto, an adherent hydrogel layer; and
   an absorbent component for storing water and arranged adjacent to said adherent layer for automatically supplying said water to said adherent hydrogel layer.

2. An electrode assembly for electrotherapy, comprising:
   a conductive component; adjacent thereto, an adherent hydrogel layer; and an absorbent component for storing water and arranged adjacent to said adherent layer for supplying said water to said adherent hydrogel layer,
   wherein said absorbent component is placed between the conductive component and the adherent hydrogel layer.

3. An assembly in accordance with claim number 2, characterized by the fact that the adherent hydrogel layer contains at least one opening situated adjacent to the absorbent component in order to allow impregnation of said absorbent component with water.

4. An assembly in accordance with claim number 3, characterized by the fact that the adherent hydrogel layer is covered with a protective sheet which contains an opening or openings situated opposite the opening or openings provided within the adherent hydrogel layer, in order to allow impregnation of the absorbent component with water, without it being necessary to remove said protective sheet.

5. An assembly in accordance with any one of claims 1 and 2–4, characterized by the fact that an ionized active substance is added to the water which impregnates the absorbent component.

6. An assembly in accordance with claim number 2, wherein said absorbent component is fitted into a hole which is formed in said adherent hydrogel layer.

7. An electrode assembly for electrotherapy, comprising:
   a conductive component; adjacent thereto, an adherent hydrogel layer; and an absorbent component for storing water and arranged adjacent to said adherent layer for supplying said water to said adherent hydrogel layer,
   wherein said absorbent component is situated adjacent the conductive component and fitted into an area within the adherent hydrogel layer.

8. An assembly in accordance with claim number 7, characterized by that fact that the adherent hydrogel layer is covered with a protective sheet which contains an opening opposite the area where the absorbent component is situated, in order to allow replacement of the absorbent component and/or to allow supplying of water to said adherent hydrogel layer without requiring removal of the aforementioned protective sheet.

9. An assembly in accordance with claim number 7 or claim number 8, characterized by the fact that an ionized active substance is added to water which impregnates the absorbent component.

10. An assembly in accordance with claim number 9, characterized by the fact that the absorbent component is packaged and pre-impregnated with an ionized active substance.

11. An assembly in accordance with claim number 7, wherein said area is a hole which is formed in said adherent hydrogel layer.

* * * * *